US006905879B2

(12) United States Patent
Qiu et al.

(10) Patent No.: US 6,905,879 B2
(45) Date of Patent: Jun. 14, 2005

(54) ISOTOPE-CODED IONIZATION-ENHANCING REAGENTS (ICIER) FOR HIGH-THROUGHPUT PROTEIN IDENTIFICATION AND QUANTITATION USING MATRIX-ASSISTED LASER DESORPTION IONIZATION MASS SPECTROMETRY

(75) Inventors: Yongchang Qiu, Arlington, MA (US); Jack H. Wang, Lexington, MA (US); Rodney M. Hewick, Boston, MA (US)

(73) Assignee: Genetics Institute, Inc., Cambridge, MA (US)

( * ) Notice: Subject to any disclaimer, the term of this patent is extended or adjusted under 35 U.S.C. 154(b) by 647 days.

(21) Appl. No.: 10/044,708

(22) Filed: Oct. 22, 2001

(65) Prior Publication Data

US 2003/0054570 A1 Mar. 20, 2003

Related U.S. Application Data

(60) Provisional application No. 60/242,645, filed on Oct. 23, 2000.

(51) Int. Cl.$^7$ .............................................. G01N 33/00
(52) U.S. Cl. ......................... 436/86; 436/161; 436/173; 436/175; 436/56
(58) Field of Search ........................ 436/86, 161, 173, 436/174, 175, 815, 56, 59; 422/61

(56) References Cited

U.S. PATENT DOCUMENTS

| | | | |
|---|---|---|---|
| 4,977,320 A | 12/1990 | Chowdhury | |
| 5,245,186 A | 9/1993 | Chait | |
| 5,288,644 A | 2/1994 | Beavis | |
| 5,453,247 A | 9/1995 | Beavis | |
| 5,643,798 A | 7/1997 | Beavis | |
| 5,792,664 A | 8/1998 | Chait | |
| 6,629,040 B1 * | 9/2003 | Goodlett et al. | 702/23 |
| 2002/0076817 A1 * | 6/2002 | Figeys et al. | 436/6 |

FOREIGN PATENT DOCUMENTS

| | | |
|---|---|---|
| WO | WO91/04781 A1 | 4/1991 |
| WO | WO93/24834 A1 | 12/1993 |
| WO | WO00/11208 A1 | 3/2000 |
| WO | WO 02/48717 | 6/2002 |

OTHER PUBLICATIONS

E. Krause et al, "The Dominance of Arginine–Containing Peptides in MALDI–Derived Tryptic Mass Fingerprints of Proteins", Analytical Chemistry, 71(19)4160–4165 (Oct., 1999).

M. Mann, "Quantitative Proteomics?", Natue Biotechnology, 17:954–955 (Oct., 1999).

S. Sechi et al, "Modification of Cysteine Residues by Alkylation. A Tool in Peptide Mapping and Protein Identification", Analytical Chemistry, 70(24):5150–5158 (Dec., 1998).

S. Gygi et al, "Quantitative Analysis of Complex Protein Mixtures Using Isotope–Coded Affinity Tags", Nature Biotechnology, 17:994–999 (Oct., 1999).

D. Fenyo et al, "Protein Identification Using Mass Spectrometric Information", Electrophoresis, 19:998–1005 (1998), no month.

Y. Qiu et al, "Acid–Labile Isotope–Coded Extractant (ALICE) and its Use in Quantitative Mass Spectrometric Analysis of Protein Mixtures", U.S. Appl. No. 10/045,170, filed Oct. 22, 2001.

Mckendrick, et al., "Rapid Mass Spectrometric Determination of Preferred Irreversible Proteinase Inhibitors in Combinatorial Libraries", International Journal of Mass Spectrometry, 176(1–2):113–124 (1998), no month.

Brancia, et al., "Improved Matrix–Assisted Laser Desorption/Ionization Mass Spectrometric Analysis of Tryptic Hydrolysates of Proteins Following Guanidination of Lysine–Containing Peptides", Rapid Communications in Mass Spectrometry, 14(21):2070–2073 (2000), no month.

Kratzer, et al., "Suppression Effects i Enzymatic Peptide Ladder Sequencing Using Ultraviolet—Matrix Assisted Laser Desorption/Ionization—Mass Spectrometry", Electrophoresis, 19(11):1910–1919 (1998).

* cited by examiner

Primary Examiner—Maureen M. Wallenhorst
(74) Attorney, Agent, or Firm—Steven B. Kelber; DLA Piper Rudnick Gray Cary US LLP

(57) ABSTRACT

Arginine-containing cysteine-modifying compounds useful for MALDI-MS analysis of proteins are provided. These compounds termed isotope-coded ionization enhancement reagents (ICIER) can provide ionization enhancement in MALDI-MS, relative quantitation, and additional database searching constraints at the same time without any extra sample manipulation. More specifically, ICIER increase the ionization efficiency of cysteine-containing peptides by attachment of a guanidino functional group. ICIER also increase the overall hydrophilicity of these peptides due to the hydrophilic nature of ICIER and thus increase the percentage of recovery of these peptides during sample handling and processing such as in-gel digestion or liquid chromatography. Finally, a combination of both light and heavy ICIER provides an accurate way to obtain relative quantitation of proteins by MALDI-MS and additional database searching constraints (number of cysteine residues in every single peptide peak) to increase the confidence of protein identification by peptide mass mapping.

13 Claims, No Drawings

SEQUENCE LISTING

<160> NUMBER OF SEQ ID NOS: 30

<210> SEQ ID NO 1
<211> LENGTH: 12
<212> TYPE: PRT
<213> ORGANISM: Peptide of CTLA4-IgG

<400> SEQUENCE: 1

Lys Asn Gln Val Ser Leu Thr Cys Leu Val Lys Gly
1               5                   10

<210> SEQ ID NO 2
<211> LENGTH: 12
<212> TYPE: PRT
<213> ORGANISM: Peptide of CTLA4-IgG

<400> SEQUENCE: 2

Arg Ala Met Asp Thr Gly Leu Tyr Ile Cys Lys Val
1               5                   10

<210> SEQ ID NO 3
<211> LENGTH: 16
<212> TYPE: PRT
<213> ORGANISM: Peptide of CTLA4-IgG

<400> SEQUENCE: 3

Arg Gly Ile Ala Ser Phe Val Cys Glu Tyr Ala Ser Pro Gly Lys Ala
1               5                   10                  15

-continued

```
<210> SEQ ID NO 4
<211> LENGTH: 21
<212> TYPE: PRT
<213> ORGANISM: Peptide of CTLA4-IgG

<400> SEQUENCE: 4

Arg Thr Pro Glu Val Thr Cys Val Val Val Asp Val Ser His Glu Asp
1               5                   10                  15

Pro Glu Val Lys Phe
            20

<210> SEQ ID NO 5
<211> LENGTH: 25
<212> TYPE: PRT
<213> ORGANISM: Peptide of CTLA4-IgG

<400> SEQUENCE: 5

Arg Trp Gln Gln Gly Asn Val Phe Ser Cys Ser Val Met His Glu Ala
1               5                   10                  15

Leu His Asn His Tyr Thr Gln Leu Ser
            20                  25

<210> SEQ ID NO 6
<211> LENGTH: 10
<212> TYPE: PRT
<213> ORGANISM: Peptide of Interleukin (IL) - 12

<400> SEQUENCE: 6

Lys Thr Ser Ala Thr Val Ile Cys Arg Lys
1               5                   10

<210> SEQ ID NO 7
<211> LENGTH: 14
<212> TYPE: PRT
<213> ORGANISM: Peptide of IL-12

<400> SEQUENCE: 7

Lys Glu Phe Gly Asp Ala Gly Gln Tyr Thr Cys His Lys Gly
1               5                   10

<210> SEQ ID NO 8
<211> LENGTH: 16
<212> TYPE: PRT
<213> ORGANISM: Peptide of IL-12

<400> SEQUENCE: 8

Arg Tyr Tyr Ser Ser Ser Trp Ser Glu Trp Ala Ser Val Pro Cys Ser
1               5                   10                  15

<210> SEQ ID NO 9
<211> LENGTH: 21
<212> TYPE: PRT
<213> ORGANISM: Peptide of IL-12

<400> SEQUENCE: 9

Arg Gly Ser Ser Asp Pro Gln Gly Val Thr Cys Gly Ala Ala Thr Leu
1               5                   10                  15

Ser Ala Glu Arg Val
            20

<210> SEQ ID NO 10
<211> LENGTH: 20
<212> TYPE: PRT
<213> ORGANISM: Peptide of IL-12
```

```
<400> SEQUENCE: 10

Arg Phe Thr Cys Trp Trp Leu Thr Thr Ile Ser Thr Asp Leu Thr Phe
1               5                   10                  15

Ser Val Lys Ser
            20

<210> SEQ ID NO 11
<211> LENGTH: 16
<212> TYPE: PRT
<213> ORGANISM: Peptide of alpha-Lactoalbumin

<400> SEQUENCE: 11

Lys Ala Leu Cys Ser Glu Lys Leu Asp Gln Trp Leu Cys Glu Lys Leu
1               5                   10                  15

<210> SEQ ID NO 12
<211> LENGTH: 17
<212> TYPE: PRT
<213> ORGANISM: Peptide of alpha-Lactoalbumin

<400> SEQUENCE: 12

Lys Phe Leu Asp Asp Asp Leu Thr Asp Asp Ile Met Cys Val Lys Lys
1               5                   10                  15

Ile

<210> SEQ ID NO 13
<211> LENGTH: 23
<212> TYPE: PRT
<213> ORGANISM: Peptide of alpha-Lactoalbumin

<400> SEQUENCE: 13

Lys Ile Trp Cys Lys Asp Asp Gln Asn Pro His Ser Ser Asn Ile Cys
1               5                   10                  15

Asn Ile Ser Cys Lys Asp Phe
            20

<210> SEQ ID NO 14
<211> LENGTH: 5
<212> TYPE: PRT
<213> ORGANISM: Peptide of Lysozyme

<400> SEQUENCE: 14

Arg Gly Cys Arg Leu
1               5

<210> SEQ ID NO 15
<211> LENGTH: 6
<212> TYPE: PRT
<213> ORGANISM: Peptide of Lysozyme

<400> SEQUENCE: 15

Arg Asn Arg Cys Lys Gly
1               5

<210> SEQ ID NO 16
<211> LENGTH: 11
<212> TYPE: PRT
<213> ORGANISM: Peptide of Lysozyme

<400> SEQUENCE: 16

Arg Cys Glu Leu Ala Ala Ala Met Lys Arg His
1               5                   10
```

<210> SEQ ID NO 17
<211> LENGTH: 13
<212> TYPE: PRT
<213> ORGANISM: Peptide of Lysozyme

<400> SEQUENCE: 17

Arg Cys Lys Gly Thr Asp Val Gln Ala Trp Ile Arg Gly
1               5                   10

<210> SEQ ID NO 18
<211> LENGTH: 14
<212> TYPE: PRT
<213> ORGANISM: Peptide of Lysozyme

<400> SEQUENCE: 18

Arg Trp Trp Cys Asn Asp Gly Arg Thr Pro Gly Ser Arg Asn
1               5                   10

<210> SEQ ID NO 19
<211> LENGTH: 21
<212> TYPE: PRT
<213> ORGANISM: Peptide of Lysozyme

<400> SEQUENCE: 19

Arg His Gly Leu Asp Asn Tyr Arg Gly Tyr Ser Leu Gly Asn Trp Val
1               5                   10                  15

Cys Ala Ala Lys Phe
            20

<210> SEQ ID NO 20
<211> LENGTH: 25
<212> TYPE: PRT
<213> ORGANISM: Peptide of Lysozyme

<400> SEQUENCE: 20

Arg Asn Leu Cys Asn Ile Pro Cys Ser Ala Leu Leu Ser Ser Asp Ile
1               5                   10                  15

Thr Ala Ser Val Asn Cys Ala Lys Lys
            20                  25

<210> SEQ ID NO 21
<211> LENGTH: 26
<212> TYPE: PRT
<213> ORGANISM: Peptide of Lysozyme

<400> SEQUENCE: 21

Arg Gly Tyr Ser Leu Gly Asn Trp Val Cys Ala Ala Lys Phe Glu Ser
1               5                   10                  15

Asn Phe Asn Thr Gln Ala Thr Asn Arg Asn
            20                  25

<210> SEQ ID NO 22
<211> LENGTH: 15
<212> TYPE: PRT
<213> ORGANISM: Peptide of Ribonuclease

<400> SEQUENCE: 22

Arg Glu Thr Gly Ser Ser Lys Tyr Pro Asn Cys Ala Tyr Lys Thr
1               5                   10                  15

<210> SEQ ID NO 23
<211> LENGTH: 24

-continued

```
<212> TYPE: PRT
<213> ORGANISM: Peptide of Ribonuclease

<400> SEQUENCE: 23

Arg Cys Lys Pro Val Asn Thr Phe Val His Glu Ser Leu Ala Asp Val
1               5                   10                  15

Gln Ala Val Cys Ser Gln Lys Asn
            20

<210> SEQ ID NO 24
<211> LENGTH: 27
<212> TYPE: PRT
<213> ORGANISM: Peptide of Ribonuclease

<400> SEQUENCE: 24

Lys Thr Thr Gln Ala Asn Lys His Ile Ile Val Ala Cys Glu Gly Asn
1               5                   10                  15

Pro Tyr Val Pro Val His Phe Asp Ala Ser Val
            20                  25

<210> SEQ ID NO 25
<211> LENGTH: 11
<212> TYPE: PRT
<213> ORGANISM: Peptide of Trypsinogen

<400> SEQUENCE: 25

Lys Val Cys Asn Tyr Val Ser Trp Ile Lys Gln
1               5                   10

<210> SEQ ID NO 26
<211> LENGTH: 12
<212> TYPE: PRT
<213> ORGANISM: Peptide of Trypsinogen

<400> SEQUENCE: 26

Lys Ala Pro Ile Leu Ser Asp Ser Ser Cys Lys Ser
1               5                   10

<210> SEQ ID NO 27
<211> LENGTH: 15
<212> TYPE: PRT
<213> ORGANISM: Peptide of Trysinogen

<400> SEQUENCE: 27

Lys Cys Leu Lys Ala Pro Ile Leu Ser Asp Ser Ser Cys Lys Ser
1               5                   10                  15

<210> SEQ ID NO 28
<211> LENGTH: 16
<212> TYPE: PRT
<213> ORGANISM: Peptide of Trypsinogen

<400> SEQUENCE: 28

Lys Leu Gln Gly Ile Val Ser Trp Gly Ser Gly Cys Ala Gln Lys Asn
1               5                   10                  15

<210> SEQ ID NO 29
<211> LENGTH: 18
<212> TYPE: PRT
<213> ORGANISM: Peptide of Trypsinogen

<400> SEQUENCE: 29

Lys Asp Ser Cys Gln Gly Asp Ser Gly Gly Pro Val Val Cys Ser Gly
1               5                   10                  15
```

```
-continued

Lys Leu

<210> SEQ ID NO 30
<211> LENGTH: 23
<212> TYPE: PRT
<213> ORGANISM: Peptide of Trypsinogen

<400> SEQUENCE: 30

Lys Ser Ala Tyr Pro Gly Gln Ile Thr Ser Asn Met Phe Cys Ala Gly
1               5                   10                  15

Tyr Leu Glu Gly Gly Lys Asp
            20
```

ISOTOPE-CODED IONIZATION-ENHANCING REAGENTS (ICIER) FOR HIGH-THROUGHPUT PROTEIN IDENTIFICATION AND QUANTITATION USING MATRIX-ASSISTED LASER DESORPTION IONIZATION MASS SPECTROMETRY

CROSS-REFERENCE TO RELATED APPLICATIONS

This application claims the benefit of the priority of U.S. Provisional Patent Application No. 60/242,645, filed Oct. 23, 2000.

BACKGROUND OF THE INVENTION

The present invention relates to the field of high-throughput protein analysis. More specifically, this invention relates to novel reagents for use in the identification and quantitation of proteins using matrix-assisted laser desorption/ionization mass spectrometry (MALDI-MS) in combination with peptide mass fingerprinting or fragment ion-based database searching.

MALDI-MS has become an established tool for the rapid identification of isolated proteins and has been used inter alia to identify proteins involved with human cancers, to elucidate components of multi-protein complexes, as well as for large-scale identification of proteins in organisms with fully sequenced genomes. Prior to MALDI-MS analysis, proteins/peptides are first separated by one-dimensional or two-dimensional polyacrylamide gel electrophoresis (1D or 2D-PAGE) or multidimensional liquid chromatography. Proteins/peptides are then identified by peptide mass mapping or fragment ion based database searching. Analytical procedures involving MALDI-MS are very robust, easy to automate, and most importantly, very fast both in terms of data acquisition and analysis.

However, peptide mass mapping may not routinely yield unambiguous protein identification with high confidence levels, particularly when only a few peptides are encountered. Furthermore, MALDI-MS often yields lower sequence coverage of proteins analyzed than electrospray ionization mass spectrometry (ESI-MS). This lower sequence coverage primarily results from both poor recovery of hydrophobic peptides during sample preparation and inefficient ionization of peptides without arginine residues by MALDI. In addition, MALDI-MS is intrinsically poor as a quantitation tool. Thus, it is very difficult to measure the relative abundance of proteins directly using MALDI-MS data.

There is a need in the art for additional reagents and methods for improving performance of MALDI-MS analysis of proteins/peptides both in terms of confident identification and accurate quantitation.

SUMMARY OF THE INVENTION

In one aspect, the invention provides a method for accurate relative quantitation of proteins using MALDI-MS. This method involves the following steps: reducing the disulfide bonds of proteins from a biological mixture; reacting the samples to be compared with a compound containing a guanidino group attached to a thiol reactive group via a linker which can be differentially labeled with either heavy or light isotopes (optionally prior to or following reduction); separating the proteins from the mixture; digesting the proteins; and subjecting them to quantitative mass spectrometric analysis. The compounds of the invention are also well suited for enhancing ionization efficiency of cysteine-containing peptides by MALDI-MS. This method is performed using the steps described above, with the following additional steps. The first sample is labeled with a reagent with isotopic substitutions and a second sample (e.g., a reference) is labeled with the equivalent reagent lacking these isotopic substitutions. Thereafter, the samples, or aliquots thereof, are mixed, prior to the separation step. After mixing, the modified proteins may be separated by 1D- or 2D-PAGE, gel bands or spots are cut and subjected to in-gel enzymatic digestion and subsequently MALDI-MS analysis. Alternatively, the mixed modified proteins may be subjected to enzymatic digestion and then the resulted peptides separated by various chromatographic steps before being subjected to MALDI-MS analysis. The proteins may be identified by peptide mass mapping or fragment-ion based data analysis and the relative protein abundance may be obtained by analyzing the relative peak intensity or peak area of the same peptide from two different samples.

In another aspect, the invention also provides a method for accurate relative quantitation and identification of proteins analyzed by electrospray MS. This method is performed in a manner similar to the method described above.

In yet another aspect, the invention provides novel reagents and reagent kits containing the compounds of the invention.

Other aspects and advantages of the present invention are described further in the following detailed description of the preferred embodiments thereof

DETAILED DESCRIPTION OF THE INVENTION

The inventors have identified a number of problems that cause the ambiguous results in both identification and relative quantitation of proteins using conventional approaches involving gel electrophoresis, MALDI-MS, and peptide mass mapping. More specifically, the inventors have found that the conventional 2D-PAGE/MALDI-MS/peptide mass mapping approach often provides inaccurate quantitation of proteins by gel image analysis and often ambiguous protein identifications. The inventors believe that poor ionization of certain peptides by MALDI is one of the main causes for ambiguous protein identifications. The present invention provides reagents and methods which overcome the defects in conventional MALDI-MS and peptide mass mapping methods.

Advantageously, the reagents of the invention can be used as cysteine-alkylating reagents, which provide many more peptide peaks in MALDI-MS than reagents previously described for use in MALDI-MS. This increase in peptide peaks observed when utilizing the reagents of the invention is due to the increased hydrophilicity and better ionization efficiency provided to the cysteine-containing peptides. Furthermore, because the methods of the invention utilize a mixture of light and heavy reagents, the exact number of cysteine residues in all peptide peaks observed by MALDI-MS can be determined. The resulting higher protein sequence coverage (more peptides observed) together with the knowledge of the exact number of cysteine residues in all peptides observed greatly increases the specificity of database searching using peptide mass fingerprinting. In fact, this additional information can make peptide mass fingerprinting routinely yield confident protein identifications and therefore makes the MALDI-MS combined with peptide mass fingerprinting a true high-throughput and yet unambiguous protein identification tool. The higher protein sequence coverage also permits a more complete chemical modification map of proteins to be obtained. Furthermore, the differential labeling strategy improves the currently popular 2D-PAGE-MS or 2D-LC-MS approaches in proteomics by increasing the dynamic range and accurately quantifying individual proteins. This improvement provides a much more complete picture of any proteome through the use of 2D-PAGE/2D-LC and MALDI-MS, thus increasing the possibility of finding protein drug targets that are differentially expressed in disease states.

Thus, the reagents of the invention are advantageous over conventional reagents for MALDI-MS analysis of proteins. These reagents can also be used for a variety of other purposes. These reagents and uses therefore are described in more detail below.

Compounds With Guanidino Functional Groups

Cysteine-containing peptides are often more hydrophobic due to the fact that disulfide bonds are usually buried inside of the globular proteins. Advantageously, the novel cysteine-modifying reagents of the invention not only increase the hydrophilicity of cysteine-containing peptides and thus minimize the loss of these hydrophobic peptides/proteins but also, more importantly, increase the ionization efficiency of these peptides by attachment of a guanidino functional group. Although not limited to such a use, these compounds are particularly well suited for use in MALDI-MS analysis.

In one embodiment, the compounds of the invention (ICIER) has a formula of A1-Linker-A2 which comprises a reactive group (A1) attached to an ionization enhancement group (A2) via a linker which can be differentially labeled with stable isotopes (Linker). Suitably, the ionization enhancement group is a strong basic functionality. In one embodiment, the ionization enhancement group (A2) is a guanidino group and has the formula: —NH—C(NH)—NH$_2$.

The linker is any structure which may be differentially labeled with stable isotopes for use in quantitation and identification of proteins using MALDI-MS. In one embodiment, the linker contain from 1 to 100 atoms in length, about 3 to about 50 atoms in length, or about 5 to about 15 atoms in length, which are composed of carbon, and optionally, one or two atoms selected from O, S, NH, NR, NR', CO, C(O)O, C(O)S, S—S, SO$_2$, C(O)—NR', CS—NR', or Si—O. Optionally, one or more of the C atoms may be substituted with a small alkyl (C$_1$-C$_6$), alkenyl, alkoxy, aryl, or diaryl groups. For example, the linker may be an alkyl, alkenyl, or alkynyl group, optionally substituted as described above. In another example, the linker may itself contain one or more O, S, NH, NR, NR', CO, C(O)O, C(O)S, S—S, SO$_2$, C(O)—NR', CS—NR', Si—O groups bound to one or more C atoms, which may be optionally substituted. In one embodiment, the linker is an alkyl group which contains a substitution of about four to about twelve atoms with a stable isotope. However, the linker may contain more than six isotope substitutions where desirable. For example, for peptides at the higher end of the molecular weight range at which MS is useful (e.g., about 2000 Da to 3500 Da) it may be desirable for the linker to contain eight, ten, twelve or more substitutions, in order to achieve the differential analysis required; whereas peptides at the lower end of the molecular weight range for MS (e.g., about 500 to 2000 Da) may require only four to six substitutions. For the selected number of substitutions, any one or more of the hydrogen, nitrogen, oxygen, carbon, or sulfur atoms in the linker may be replaced with their isotopically stable isotopes: $^2$H, $^{13}$C, $^{15}$N, $^{17}$O, $^{18}$O, or $^{34}$S.

The reactive group A1 reacts, preferably specifically, with thiols, and more particularly, with cysteine residues. Desirably, the thiol-reactive group is selected from the group consisting iodide, maleimide (see, for example, the structures below)

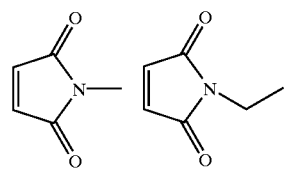

or α-haloacetyl groups such as X—CH$_2$CO—. Most suitably, the X is selected from halogens such as iodine, bromine, and chorine to form iodoacetyl, bromoacetyl, or chloroacetyl functionalities.

In another alternative, the thiol-reactive group may be selected from other α-, β-conjugated double bond structures, such as

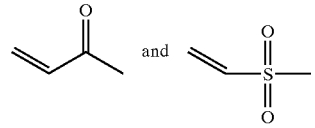

and the like. Still other reactive groups can be readily synthesized to contain other thiol-specific reactive groups for use in binding cysteine-containing peptides.

In certain preferred embodiments, a compound of the invention (ICIER) comprises a thiol-reactive group attached to a guanidino group by a linker, in which the formula of the compound is:

Reagent A:

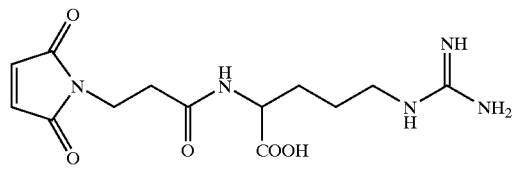

Reagent B:

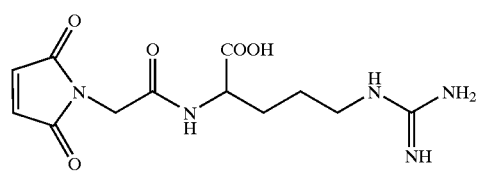

Reagent C:

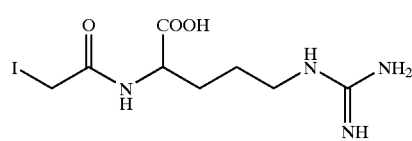

Reagent C¢:

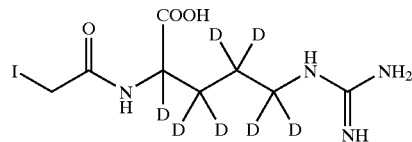

Reagent D:

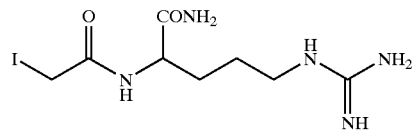

While Compound C' (one example of heavy ICIER) represents one particularly desirable isotopically heavy substituted version of Compound C (one example of Light ICIER), other isotopically heavy versions of this formula may be readily produced according to the present invention. Similarly, a variety of substitutions to Compounds A, B and D may be readily generated by one of skill in the art based on the teachings provided herein.

Synthesis of Reagents

The compounds of the invention may be readily synthesized by one of ordinary skill in the art utilizing the methods described in the examples below and techniques known to those of skill in the art. Some exemplary methods are illustrated in Example 1 below.

For example, a suitable starting material may be mixed with L-arginine in a mixture of tetrahydrofuran (THF) and water in a ratio of about 1 to about 1 parts by volume, for about 10 to about 48 hours, and most preferably about 16 hours at room temperature. The reaction mixture is then poured into acetone and the solid is collected. The solid is then dissolved in water and introduced into a suitable column, which is eluted with water to provide a compound of the invention. However, the invention is not so limited. For example, other suitable solvents may be substituted for the THF or acetone. Alternatively, the ratio of THF to water may be adjusted, as needed or desired. As another example, a salt of L-arginine (e.g., L-arginine D7-hydrochloride or L-argininamide dihydrochloride) may be dissolved in water and the pH adjusted to the basic range (e.g., about 8 to about 13, and more preferably about 8 to about 10), prior to reaction with iodoacetyl anhydride. Thereafter, the acid may be collected, e.g., by lowering the pH to the acid range (e.g., about 2 to about 4), filtering the resin and extracting the aqueous solution, followed by further filtration. The resulting solid may be freeze-dried to yield the desired compound.

However, given the descriptions provided herein, one of skill in the art will be able to readily select appropriate techniques and reagents for synthesis of compounds of the invention.

Following synthesis, the compounds are preferably purified to achieve the best results, particularly when they will be used in conjunction with 2D-PAGE, since reagents made in situ contain an excess of salt that will interfere with the first separation step of isoelectric focusing. Suitably, purification may be performed by filtration. Alternatively, other suitable methods may be readily selected by one of skill in the art.

These compounds may be utilized in a variety of methods in which protein/peptide labeling and/or increasing the ionization of cysteine-containing peptides is desired. However, the compounds are particularly useful in methods for high-throughput protein identification and quantitation using MALDI-MS.

Methods of Using the Compounds of the Invention

The compounds of the invention are particularly useful in methods for quantitation and identification of one or more proteins in a mixture. Suitably, the peptides analyzed by the method of the invention are between about 500 Daltons (Da) to about 3500 Daltons. The protein mixture may be a sample from a cell or tissue culture, or biological fluids, cells or tissues. Samples from a culture include cell homogenates and cell fractions. Biological fluids include urine, blood (including, e.g., whole blood, plasma and sera), cerebrospinal fluid, tears, feces, saliva, and lavage fluids. The mixtures may include proteins, lipids, carbohydrates, and nucleic acids. The methods of the invention employ MS and $(MS)^n$ methods. Currently, matrix assisted laser desorption ionization MS (MALDI/MS) and electrospray ionization MS (ESI/MS) methods are preferred. However, a variety of other MS and $(MS)^n$ techniques may be selected.

In one embodiment, the invention provides a method for quantitative analysis of a proteome (i.e., a complex mixture containing proteins and/or peptides) using the compound of the invention. Typically, a sample is obtained from a source, as defined above. Where isolated proteins will be identified using techniques based on MALDI-MS and peptide mass mapping, the sample may be compared to a reference protein mixture, which is obtained as a sample from the same source or may be obtained from another source. Alternatively, isolated proteins may be identified using post-source delay (PSD) or collision-induced dissociation (CID) techniques followed by fragment ion-based database searching (M. Mann and M. Wilm, *Anal. Chem.*, 66: 4390 (1994)) or de novo sequencing, and the sample may be compared to a reference protein mixture using MS data. The sample protein mixture and the reference protein mixture are processed separately, applying identical reaction conditions, with the exception that only one mixture (e.g., the sample) will be reacted with the compound containing isotopically stable isotopes. Alternatively, where relative quantitation of proteins is not desirable, no reference samples are required; nor are isotopically heavy equivalents of the compounds of the invention required. Optionally, any labeling reaction step may be performed prior to, or following, the other method steps which are described herein.

Typically, the protein sample is dissolved in a buffer suitable for 1D-PAGE or 2D-PAGE or in-solution enzymatic digestion. Such buffers may be purchased commercially from a variety of sources (e.g., Genomic Solutions, Ann Arbor, Mich.; BioRad, Hercules, Calif.) or prepared according to known methods. Throughout the following method steps, the pH of the mixture is maintained under neutral or basic conditions. Most suitably, the pH is maintained between 7 and 10. Preferably, the method of the invention is performed at a basic pH where the compound of the invention containing the guanidino group (e.g., compounds A, B, C, C' and D) is utilized. Most suitably, the pH is in the range of about 8 to about 9, and most preferably about 8.5. Alternatively, the method of the invention is preferably performed at a neutral pH where a compound of the invention containing a maleimide affinity tag is utilized. In this circumstance, the method is preferably performed at a pH of about 6.5 to about 8.5, more preferably 7 to 8, and most preferably 7 to 7.5.

Following preparation of the sample and reference, the disulfide bonds of the proteins in the sample(s) or reference mixtures are reduced to free SH groups. Suitable reducing agents include tri-n-butylphosphine, mercaptoethylamine, dithiothreitol (DTT), and tricarboxyethylphosphine, which are used in excess. However, other suitable reducing agents may be substituted. In one embodiment, disulfide bonds are denatured using 50 mM Tris buffer, 6M guanidine HCl, 5 mM tributyl phosphine at pH 8.5 for 1 hour at 37° C. However, other reducing agents, buffered to a pH in the basic range may be selected and incubated for varying lengths of times at room temperature.

Where no protein quantitation is to be performed, no reference sample need be labeled, and the following parallel reaction steps with equivalent heavy or light ICIER and mixing steps can be eliminated. Where protein quantitation will be performed, a selected compound of the invention, either an isotopically heavy or light compound, will be reacted with the samples to be compared. This labeling reaction step may be performed prior to, or following, the other method steps which are described herein. Typically, the reference sample is labeled with the isotopically heavy compound and the experimental sample(s) are labeled with the isotopically light form of the compound. However, the labeling may be reversed. Following reduction and reaction with the selected labeling reagents (heavy or light ICIER), defined aliquots of the samples (optionally labeled with isotopically different compounds, e.g., corresponding light and heavy compounds) are combined and all the subsequent steps are performed on the pooled samples. Preferably, equal amounts of the samples are combined.

Suitably, prepared gels for one-dimensional (1D) or two-dimensional (2D) polyacrylamide gel electrophoresis (PAGE) may be obtained from a variety of commercial sources and used according to manufacturer's instruction (Genomics Solutions; Ann Arbor, Mich.; NOVEX, San Diego, Calif.). However, the invention is not so limited. One of skill in the art can readily apply other techniques for separating the ICIER-labeled proteins.

Following mixing of the ICIER-treated samples, the proteins are separated by 1D-PAGE or 2D-PAGE. Then the protein bands or spots of interest are cut and subjected to enzymatic digestion. Suitably, the proteins may be subjected to in-gel digestion using techniques which have been described previously (e.g., Rosenfeld et al, *Anal. Biochem.*, 203:173–179 (1992) and Sechi et al, *Anal. Chem.*, 70:5150–5158 (1998)), or the modification thereof as described in the examples below.

A suitable protease for use in this enzymatic digestion method may be readily selected from among proteases which are compatible with the basic conditions and the procedure. In one embodiment, the protease is trypsin. In another embodiment, a mixture of proteases which have similar activity levels at basic pH is used. Such proteases may include aminopeptidases, carboxypeptides, among others. Alternatively, protein digestion may be omitted where the proteins to be analyzed are small (e.g., about 500 to 1000 Da).

Suitably, the peptides are extracted from the gel using conventional techniques. For example, following destaining, the peptides may be extracted by adding a solution of acetonitrile and trifluoroacetic acid (TFA) to the gel band and incubating, before collecting the liquid phase. This step may be repeated and additional acetonitrile added to complete the extraction. The extract solutions are pooled and dried, then reconstituted with a solution of acetonitrile and TFA. Other suitable methods for peptide extraction are well known to those of skill in the art and may be readily utilized.

The isolated, derivatized peptides are then analyzed using MS techniques. Both the relative quantity and sequence identity of the proteins from which the labeled peptides originated can be determined by MALDI-MS techniques (i.e. MS and MS$^n$(PSD, CID)) and subsequent data analysis (i.e. peptide mass mapping or fragment-ion based data analysis). Preferably, the relative quantitation of proteins is obtained from MS data, while the protein identification can derived from the analysis of either MS data (peptide mass mapping) or MS$^n$ data (fragment ion based database searching).

Apparatuses for performing MALDI-MS, and techniques for their use, are described in International Publication WO 93/24835, U.S. Pat. No. 5,288,644, R. Beavis and B. Chait, *Proc. Natl. Acad. Sci. USA,* 87:6873–6877 (1990); B. Chait and K. Standing, Int. *J. Mass Spectrom, Ion Phys.,* 40:185 (1981) and Mamyrin et al, *Sov. Phys. JETP,* 37:45 (1973), all of which are incorporated by reference herein. Briefly, the frequency tripled output of, e.g., a Q-switched Lumonics HY400 neodymium/yttrium aluminum garnet lawer ("Nd-YAG") (355 nm, 10-nsec output pulse) is focused by a lens (12-inch focal length) through a fused silica window onto a sample inside the mass spectrometer. The product ions formed by the laser are accelerated by a static electric potential of 30 kV. The ions then drift down a 2-m tube maintained at a vacuum of 30 $\mu$Pa and their arrival at the end of the tube is detected and recorded using, e.g., a Lecroy TR8828D transient recorder. The transient records of up to 200 individual laser shots are summed together and the resulting histogram is plotted as a mass spectrum. Peak centroid determinations and data reduction can be performed using a VAX workstation or other computer system.

However, other MS techniques, including electrospray ionization (ESI)/MS, among others, may be readily utilized to analyze the proteins and peptides modified by the compounds of the invention (ICIER).

Reagent Kit

The invention further provides a reagent kit for the analysis of proteins by mass spectral analysis. Typically, such a kit will contain one or more compounds of the invention. Most suitably, the kit will contain a set of substantially identical, differentially labeled (isotopically light and heavy) compounds. The kit may further contain one or more proteolytic enzymes, reaction buffers, or wash solutions.

The method and kit of the invention may be used for a variety of clinical and diagnostic assays, in which the presence, absence, deficiency or excess of a protein is associated with a normal or disease state. The method and kit of the invention can be used for qualitative and quantitative analysis of protein expression in cells and tissues. The method and kit can also be used to screen for proteins whose expression levels in cells or biological fluids is affected by a drug, toxin, environmental change, or by a change in condition or cell state, e.g., disease state, malignancy, site-directed mutation, gene therapy, or gene knockouts.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

Reagents of the Invention

This example illustrates methods for synthesis of exemplary compounds A, B, C, C' and D of the invention. These compounds are useful as reagents in MALDI-MS and peptide mass mapping, as shown in the following examples.

1. 2-(2-(2,5-dioxo-2,5-dihydro-pyrrol-1-yl)-acetylamino)-5-guanidino-pentanoic Acid or Maleimidoacetyl Arginine (A):

(2,5-Dioxo-2,5-dihydro-pyrrol-1-yl)-acetic acid-2,5-dioxo-pyrrolidin-1-yl ester (4.8 g, 19 mmol) and L-arginine (2.9, 17 mmol) was stirred in 30 mL of a mixture of tetrahydrofuran (THF) and water, THF:H$_2$O (1:1), for 16 hours at room temperature. The reaction mixture was poured into acetone (1.5 L) and the solid was collected. The solid was dissolved in H$_2$O (3 mL) and then introduced onto Bakerbond (Octadecyl (C18) 40 $\mu$m prep LC Packing) column, and eluted with water to give 1.1 g of product. $^1$H NMR (D$_2$O, 300 MHZ): 6.8 (s, 2H), 4.3 (H$_a$, d, J=16.9 Hz, 1H), 4.2 (H$_b$, d, J=16.9 Hz, 1H), 4.1 (dd, J=4.9, 7.7 Hz, 1H), 3.1 (t, J=6.9 Hz, 2H), 1.8-1.5 (m, 4H).

2. 2-(3-2,5-dioxo-2,5-dihydro-pyrrol-1-yl)-propionylamino)-5-guanidino-pentanoic Acid or Maleimidopropionyl Arginine (B):

3-(2,5-dioxo-2,5-dihydro-pyrrol-1-yl)-propionic acid-2,5-dioxo-pyrrolidin-1-yl ester (7.6 g, 28.5 mmol) and L-arginine (4.3 g, 25 mmol) was stirred in 50 mL of a mixture of THF:H$_2$O (1:1) for 16 hr at room temperature. The reaction mixture was poured into acetone (1.5 L) and the solid was collected. The solid was dissolved in H$_2$O (5 mL) and then introduced onto Bakerbond (Octadecyl (C18) 40 $\mu$m prep LC Packing) column, and eluted with water to give 1.5 g of product. $^1$H NMR (D$_2$O, 300 MHZ): 6.8 (s, 2H), 4.1 (dd, J=4.7, 7.4 Hz, 1H), 3.8 (m, 2H), 3.2 (t, J=6.9 Hz, 2H), 2.5 (m, 2H), 1.7-1.5 (m, 4H).

3. N-α-(Iodoacetyl)-L-arginine (C):

L-Arginine (8.0 g, 45.6 mmol) was dissolved in deionized water (75 mL) and was reacted with iodoacetic anhydride (21.0 g, 59.3 mmol) with vigorous stirring for 15 min while the pH was maintained between 8 and 9.5 with Dowex 1x2-100 (OH⁻). The pH was allowed to drop to ~4 (5–10 min) and 55% aqueous hydriodic acid was added to bring the pH to 2. The resin was filtered and the aqueous hydriodic acid was extracted with diethyl ether (3×250 ml). The aqueous layer was neutralized with Dowex 1x2-100 (OH⁻) to pH 8–9, the resin was filtered and washed with water and the resulting solution was freeze-dried to afford N-α-(Iodoacetyl)-L-arginine (11.9 g, 76% overall yield) as a fluffy white powder. $^1$H NMR (D$_2$O) δ 1.52–1.88 (m, 4H), 3.12 (t, 2H, J=6.7 Hz), 3.76 (d, 1H, J=10.2 Hz), 3.76 (d, 1H, J=10.4 Hz), 4.06–4.10 (m, 1H); $^{13}$C NMR (D$_2$O) δ-2.0, 24.5, 28.8, 40.7, 55.1, 156.8, 171.5, 178.3. Molecular formula: $C_{18}N_{15}N_4IO_3$.

4. N-α-(Iodoacetyl)-L-arginine-D$_7$ (C'):

L-arginine-D$_7$ hydrochloride (5.2 g, 28.73 mmol) was dissolved in deionized water (50 mL) and the pH was adjusted to 8 with Dowex 1x2-100 (OH⁻). It was then reacted with iodoacetic anhydride (15.5 g, 43.78 mmol) as above to afford N-α-(Iodoacetyl)-L-arginine-D$_7$ (5.5 g, overall yield 55%/o) as a fluffy white powder. $^1$H NMR (D$_2$O) δ 3.74 (d, 1H, J=10.2 Hz), 3.82 (d, J=10.4 Hz). Molecular formula: $C_8H_8D_7N_4IO_3$.

5. N-α-(Iodoacetyl)-L-argininamide hydrochloride (D):

L-Argininamide dihydrochloride (10.5 g, 42.6 mmol) was dissolved in deionized water (75 mL) and the pH was adjusted to 13 with Dowex 1x2-100 (OH⁻). Then it was reacted with iodoacetic anhydride (18.0 g, 50.85 mmol) with vigorous stirring for 15 min while the pH was maintained between 8 and 9.5 with Dowex 1x2-100 (OH⁻). The pH was allowed to drop to ~4 (5–10 min) and 55% aqueous hydriodic acid was added to bring the pH to 2. The resin was filtered and the aqueous solution was extracted by diethyl ether (3×250 ml). The aqueous layer was filtered through a pad Dowex Retardion 11A8 (50 g) and washed with water. The resultant solution was freeze-dried to afford N-α-(Iodoacetyl)-L-argininamide hydrochloride (11.1 g, 69%) as a fluffy white powder. $^1$H NMR (D$_2$O) δ 1.62–2.02 (m, 4H), 3.24 (t, 2H, J=6.6 Hz), 3.79 (d, 1H, J=10.2 Hz), 3.89 (d, 1H, J=10.7 Hz), 4.27–4.31 (m, 1H); $^{13}$C NMR (D$_2$O) δ-2.7, 24.5, 28.3, 40.6, 53.6, 156.9, 172.5, 176.3. Molecular formula: $C_8H_{16}N_5IO_2 \cdot HCl$.

EXAMPLE 2

Comparative Example Demonstrating Ionization Enhancement-MALDI-MS Analysis of Six Separate Model Proteins after Treatment with Either the Reagent of the Invention (Light Icier) or a Conventional Reagent (IAA)

A. Reduction:

90 μg each of the six model proteins, CTLA-4-IgGl, Interleukin-12 (IL-12), α-Lactalbumin, Trypsinogen, Lysozyme, and Ribonuclease, were dissolved separately in 30 μL of the reaction buffer containing 5% SDS, 20% glycerol, and 750 mM Tris-HCl (pH 8.45) to obtain solutions of 3 μg/μL. To each solution was added a 200-fold excess (with regard to cysteine content per protein) of dithiothreitol (DTT). The reduction was allowed to proceed for 30 minutes at 90° C., followed by cooling of the solutions for 10 minutes.

B. Cysteine Modification:

Reagent C (light ICIER) was synthesized as described in Example 1. Each of the six proteins was alkylated using both reagent C and iodoacetamide separately. The amount of the alkylating reagent (reagent C or iodoacetamide) was equivalent to a five-fold excess with regard to the amount of DTT used in step A. The alkylations were allowed to proceed for 1 hour at room temperature. Then 0.1 μg of each protein labeled by reagent C was mixed with 0.1 μg of the same protein but alkylated by iodoacetamide. Each of the six resultant protein solutions was then mixed in a 1:1 ratio (volume to volume) with 2x Tricine loading buffer.

C. Gel Electrophoresis and Staining:

Each of the final resultant protein solutions described in Part B (each solution contains 0.2 μg of one of the six proteins) was loaded onto a 10%, 10-well Tricine mini-gel (Novex, San Diego, Calif.). The gels were run according to the manufacturer's instructions and stained with Coomassie Blue G-250.

D. In-Gel Digestion:

Automated in-gel digestion of proteins was carried out using a 96-well ProGest (Genomic Solutions, Ann Arbor, Mich.) with a procedure modified from Rosenfeld et al, Anal. Biochem., 203:173–179 (1992) and Sechi et al, Anal. Chem., 70:5150–5158 (1998). Briefly, gel bands were cut into 1×1 mm pieces and then destained by washing sequentially with 50 μL each of the following solutions: (1) 200 mM NH$_4$HCO$_3$, (2) 50% methanol/10% acetic acid; (3) 40% ethanol/water and incubated for 10 minutes for each step. The three washing steps were repeated 5 times and then 100 μL of 10 nM NH$_4$HCO$_3$ was added and incubated for 10 minutes. The gel pieces were then dehydrated by addition of 2×100 μL of acetonitrile. After removing the excess acetonitrile, the gels were rehydrated with 25 μL of a solution containing 625 ng of trypsin in 10 mM NH$_4$HCO$_3$ and incubated at 37° C. for 10 hours. Peptides were extracted by adding 30 μL of a solution of 50% acetonitrile/0.5% trifluoroacetic acid (TFA) and incubated for 10 minutes before collecting the liquid phase. This step was repeated one more time and then 30 μL of acetonitrile was added to complete the extraction. The extracted solutions were pooled together and dried completely with a SpeedVac (Savant, Holbrook, N.Y.). Finally, the dried peptide samples were reconstituted with 20 μL of an acetonitrile/water/TFA (50:50:1) solution.

E. MALDI Mass Spectrometry

Molecular weights of all peptides were determined by analyzing one-twentieth of the reconstituted peptide solution employing a matrix-assisted laser desorption ionization (MALDI) delayed extraction (DE) reflectron time-of-flight (TOF) instrument (Voyager DE-STR, PE Biosystems, Framingham, Mass.) equipped with a nitrogen laser (337 nm) in reflectron mode. Peptides were crystallized by mixing 0.8 μL of the sample solution with 0.8 PL of a matrix solution containing saturated α-cyano-4-hydroxycinnamic acid in 0.5% TFA/50% acetonitrile/water. Spectra were externally calibrated using a mixture of known peptides.

Peak tables were generated from each spectrum and the data were used to create the ionization enhancement and peak ratio tables presented herein.

The following tables summarize the results of the MALDI-MS analysis of the six protein samples after treatment with reagent C (ICIER) or iodoacetamide (IAA) and the comparison of the same. See Tables I–XVIII.

TABLE I

CTLA4-alkylated with IAA 1:1 (1:1 @ 0.1 g/band)

| Detected Mass (Da) | Theoretical Mass (Da) | Height |
|---|---|---|
| 1161.6112 | 1161.6302 | 1991 |
| N/A | 1171.5491 | N/A |
| 1187.5239 | 1187.5441 | 1452 |
| 1485.7119 | 1485.7048 | 7944 |
| 2138.9793 | 2139.028 | 7551 |
| 2801.3180 | 2801.2677 | 1253 |
| 2817.9851* | 2817.2626 | 1567 |

Theoretical Number of Cysteines: 11
Number of Cysteines Detected: 5

TABLE II

CTLA4-IgG alkylated with Reagent C (1:1 @ 0.1 g/band)

| Detected Mass (Da) | Theoretical Mass (Da) | Height |
|---|---|---|
| 1318.7222 | 1318.7153 | 10610 |
| 1328.6746 | 1328.6343 | 3035 |
| 1344.6331 | 1344.6292 | 3922 |
| 1642.7809 | 1642.7899 | 22134 |
| 2296.0863 | 2296.1131 | 8587 |
| 2958.3574 | 2958.3528 | 1442 |
| 2974.3377 | 2974.3477 | 1210 |

Theoretical Number of Cysteines: 11
Number of Cysteines Detected: 5

TABLE III

Comparison of Data for CTLA4-IgG

| Height Ratio for CTLA4-IgG (Reagent C/IAA) | Peptide Sequence | SEQ ID NO: |
|---|---|---|
| 5.33 | (K)NQVSLTCLVK(G) | 1 |
| N/A | (R)AMDTGLYICK(V) | 2 |
| 2.70 | (R)AMDTGLYICK(V) | 2 |
| 2.79 | (R)GIASFVCEYASPGK(A) | 3 |
| 1.14 | (R)TPEVTCVVVDVSHEDPVK(F) | 4 |
| 1.15 | (R)WQQGNVFSCSVMHEALHNHYTQL(S) | 5 |
| 0.77 | (R)WQQGNVFSCSVMHEALHNHYTQK(S) | 5 |

TABLE IV

IL-12 alkylated with IAA (1:1 @ 0.1 g/band)

| Detected Mass (Da) | Theoretical Mass (Da) | Height |
|---|---|---|
| N/A | 907.4671 | N/A |
| 1412.5917 | 1412.5905 | 6566 |
| N/A | 1795.7274 | N/A |
| 1863.8916 | 1863.8507 | 6089 |
| 2206.1381 | 2206.0895 | 782 |

Theoretical Number of Cysteines: 9
Number of Cysteines Detected: 3

TABLE V

IL-12 alkylated with Reagent C (1:1 @ 0.1 g/band)

| Detected Mass (Da) | Theoretical Mass (Da) | Height |
|---|---|---|
| 1064.5402 | 1064.5523 | 2411 |
| 1569.7046 | 1569.6756 | 9028 |
| 1952.8747 | 1952.8125 | 5441 |
| 2020.9710 | 2020.9358 | 4543 |
| 2363.2748 | 2363.1746 | 1181 |

Theoretical Number of Cysteines: 9
Number of Cysteines Detected: 5

TABLE VI

Comparison of Data for IL-12

| Height Ratio for IL-12 (Reagent C/IAA) | Peptide Sequence | SEQ ID NO: |
|---|---|---|
| N/A | (K)TSATVICR(K) | 6 |
| 1.37 | (K)EFGDAGQYTCHK(G) | 7 |
| N/A | (R)YYSSSWSEWASVPCS(-) | 8 |
| 0.75 | (R)GSSDPQGVTCGAATLSAER(V) | 9 |
| 1.51 | (R)FTCWWLTTISTDLTFSVK(S) | 10 |

TABLE VII

α-Lactoalbumin alkylated with IAA (1:1 @ 0.1 g/band)

| Detected Mass (Da) | Theoretical Mass (Da) | Height |
|---|---|---|
| none | 707.3398 | N/A |
| 1091.51432 | 1091.5196 | 6131 |
| none | 1715.7508 | N/A |
| 1779.83739 | 1779.8410 | 3436 |
| none | 1843.8458 | N/A |
| 1892.92914 | 1892.9250 | 7606 |
| 2003.914 | 2003.8187 | overlap |
| 2591.27206 | 2591.1077 | 3115 |

Theoretical Number of Cysteines: 8
Number of Cysteines Detected: 5

TABLE VIII

α-Lactoalbumin alkylated with Reagent C (1:1 @ 0.1 g/band)

| Detected Mass (Da) | Theoretical Mass (Da) | Height |
|---|---|---|
| 864.42181 | 864.4249 | 6976 |
| 1248.60859 | 1248.6047 | 33460 |
| 1872.83547 | 1872.8359 | 17483 |
| 2093.96824 | 2094.0112 | 3307 |
| 2000.93299 | 2000.9309 | 11339 |
| 2207.10324 | 2207.0953 | 7629 |
| 2317.96953 | 2317.989 | 5207 |
| none | 3062.3631 | N/A |

Theoretical Number of Cysteines: 8
Number of Cysteines Detected: 7

TABLE IX

Comparison of Data for α-Lactoalbumin

| Height Ratio for α-Lactoalbumin (Reagent C/IAA) | Peptide Sequence | SEQ ID NO: |
|---|---|---|
| N/A | (K)ALCSEK(L) | aa 1–8 of SID NO:11 |
| 5.46 | (K)LDQWLCEK(L) | aa 7–16 of SID NO:11 |
| N/A | (K)FLDDDLTDDIMCVK(K) | aa 1–16 of SID NO:12 |
| 0.96 | (K)ALCSEKLDQWLCEK(L) | 11 |
| N/A | (K)FLDDDLTDDIMCVKK(I) | 12 |
| 1.00 | (K)ALCSEKLDQWLCEKL(-) | 11 |
| N/A | (K)DDQNPHSSNICNISCDK(F) | aa 5–23 of SID NO:12 |
| N/A | (K)IWCKDDQNPHSSNICNISCDK(F) | 13 |

TABLE X

Lysozyme alkylated with IAA (1:1 @ 0.1 g/band)

| Detected Mass (Da) | Theoretical Mass (Da) | Height |
|---|---|---|
| N/A | 505.2557 | N/A |
| none | 577.2880 | N/A |
| 993.4044 | 993.4001 | 16094 |
| 1065.4958 | 1065.5185 | 5466 |
| 1325.6148 | 1325.6312 | 7685 |
| 1333.6643 | 1333.6687 | 25788 |
| N/A | 1491.6552 | Buried |
| 2181.0465 | 2181.0300 | 8876 |
| 2508.5231 | 2508.29788 | 2902 |
| 2735.4461 | 2735.2636 | 2672 |

Theoretical Number of Cysteines: 9
Number of Cysteines Detected: 5

TABLE XI

Lysozyme alkylated with Reagent C (1:1 @ 0.1 g/band)

| Detected Mass (Da) | Theoretical Mass (Da) | Height |
|---|---|---|
| 662.3187 | 662.3408 | 11061 |
| 734.3755 | 734.3732 | 2407 |
| 1150.4807 | 1150.4852 | 9782 |
| 1222.5917 | 1222.6036 | 9199 |
| 1428.6595 | 1428.7164 | 56959 |
| 1490.7545 | 1490.7538 | 24700 |
| 1648.7478 | 1648.7403 | 8750 |
| 2338.1091 | 2338.1151 | 5656 |
| 2979.3921 | 2979.4450 | 1867 |

TABLE XI-continued

Lysozyme alkylated with Reagent C (1:1 @ 0.1 g/band)

| Detected Mass (Da) | Theoretical Mass (Da) | Height |
|---|---|---|
| 2892.4820 | 2892.3487 | 2113 |

Theoretical Number of Cysteines: 9
Number of Cysteines Detected: 8

TABLE XII

Comparison of Data for Lysozyme

| Height Ratio for Lysozyme (Reagent C/IAA) | Peptide Sequence | SEQ ID NO: |
|---|---|---|
| N/A | (R)GCRL(-) | 14 |
| N/A | (R)NRCK(G) | 15 |
| 0.61 | (R)WWCNDGR(T) | aa 1-9 of SID NO:18 |
| 1.68 | (R)CELAAAMKR(H) | 16 |
| 7.41 | (R)GYSLGNWVCAAK(F) | aa 1-14 of SID NO:21 |
| 0.96 | (R)CKGTDVQAWIR(G) | 17 |
| N/A | (R)WWCNDGRTPGSR(N) | 18 |
| 0.64 | (R)HGLDNYRGYSLGNWVCAAK(F) | 19 |
| 0.64 | (R)NLCNIPCSALLSSDITASVNCAK(K) | 20 |
| 0.79 | (R)GYSLGNWVCAAKFESNFNTQATNR(N) | 21 |

TABLE XIII

Ribonuclease A alkylated with IAA (1:1 @ 0.1 g/band)

| Detected Mass (Da) | Theoretical Mass (Da) | Height |
|---|---|---|
| 1504.6742 | 1504.6825 | 6041 |
| 2224.0861 | 2224.1065 | 22526 |
| 2517.2230 | 2517.2890 | 14079 |
| 2867.4150 | 2867.5666 | 4222 |

Theoretical Number of Cysteines: 8
Number of Cysteines Detected: 4

TABLE XIV

Ribonuclease A alkylated with Reagent C (1:1 @ 0.1 g/band)

| Detected Mass (Da) | Theoretical Mass (Da) | Height |
|---|---|---|
| 1661.7593 | 1661.7785 | 16953 |
| 2381.1712 | 2381.1743 | 46801 |
| 2831.3933 | 2831.3889 | 9332 |
| 3024.5002 | 3024.7205 | 4879 |

Theoretical Number of Cysteines: 8
Number of Cysteines Detected: 5

TABLE XV

Comparison of Data for Ribonuclease

| Height Ratio for Ribonuclease (Reagent C/IAA) | Peptide Sequence | SEQ ID NO: |
|---|---|---|
| 2.81 | (R)ETGSSKYPNCAYK(T) | 22 |
| 2.08 | (K)HIIVACEGNPYVPVHFDASV(-) | aa 7-27 of SID No.24 |
| 0.66 | (R)CKPVNTFVHESLADVQAVCSQK(N) | 23 |
| 1.16 | (K)TTQANKHIIVACEGNPYVPVHFDASV(-) | 24 |

TABLE XVI

Trypsinogen alkylated with IAA (1:1 @ 0.1 g/band)

| Detected Mass (Da) | Theoretical Mass (Da) | Height |
|---|---|---|
| 1168.59697 | 1168.5825 | 5577 |
| none | 1077.5250 | N/A |
| none | 1478.7347 | N/A |
| 1490.75058 | 1490.7426 | 4891 |

TABLE XVI-continued

Trypsinogen alkylated with IAA (1:1 @ 0.1 g/band)

| Detected Mass (Da) | Theoretical Mass (Da) | Height |
|---|---|---|
| 1609.68206 | 1609.6586 | 1573 |
| none | 2267.0110 | N/A |

Theoretical Number of Cysteines: 12
Number of Cysteines Detected: 3

TABLE XVII

Trypsinogen alkylated with Reagent C (1:1 @ 0.1 g/band)

| Detected Mass (Da) | Theoretical Mass (Da) | Height |
|---|---|---|
| 1325.68371 | 1325.6676 | 24135 |
| 1234.6102 | 1234.61265 | 12845 |
| 1792.94896 | 1792.9050 | 2455 |
| 1647.85269 | 1647.8277 | 14787 |
| 1923.88166 | 1923.8289 | 2795 |
| 2424.06382 | 2424.0964 | 3046 |

Theoretical Number of Cysteines: 12
Number of Cysteines Detected: 7

TABLE XVIII

Comparison of Data for Trypsinogen

| Height Ratio for Trypsinogen (Reagent C/IAA) | Peptide Sequence | SEQ ID NO: |
|---|---|---|
| 4.33 | (K)VCNYVSWIK(Q) | 25 |
| N/A | (K)APILSDSSCK(S) | 26 |
| N/A | (K)CLKAPILSDSSCK(S) | 27 |
| 3.02 | (K)LQGIVSWGSGCAQK(N) | 28 |
| 1.78 | (K)DSCQGDSGGPVVCSGK(L) | 29 |
| N/A | (K)SAYPGQITSNMFCAGYLEGGK(D) | 30 |

From these data, it was concluded that, compared to the conventional cysteine-alkylating reagent Iodoacetamide, ICIER greatly increases the ionization efficiency of cysteine-containing tryptic peptides with a lysine residue at their C-terminus. For example, in the MALDI-MS spectrum of tryptic peptides from lysozyme modified by both reagent C and IAA (see Table XII), the intensity of a peptide modified by reagent C (GYSLGNWVCAAK, aa 2–13 of SEQ ID NO:21, molecular weight, 1428.72 Da) is 7.4 times that of the same peptide modified by IAA (molecular weight, 1325.63 Da). Moreover, mass peaks for many cysteine-containing peptides with a lysine residue at their C-terminus that were absent when using IAA became well observed when using ICIER. On the other hand, ICIER modification did not have any significant effect on the ionization of peptides with an arginine residue at their C-terminus. As a result, the overall number of cysteine-containing peptides detected by MALDI-MS is also increased, and hence the sequence coverage obtained for proteins being analyzed when using ICIER is much higher than that when using iodoacetamide.

EXAMPLE 3

Protein Quantitation by Icier and MALDI-MS Using CTLA4-IgG as a Model Protein

Different amounts of CTLA4-IgG with ratios of 1:1, 1:1.5, 1:2, 1:5, and 1:10 were reduced by DTT as described in EXAMPLE 2. The samples to be compared were alkylated with either light or heavy ICIER and then mixed together before being subjected to gel electrophoresis, protein staining, in-gel digestion, and MALDI-MS analysis using the same conditions described in EXAMPLE 2.

Table XIX summarizes the labeling of CTLA4-IgG at different ratios using light and heavy ICIER. Peptide masses were all externally calibrated using default calibration files. The relative quantitation of the protein from two different pools was determined by averaging the mass intensity ratios between all seven pairs of peptides labeled by light and heavy ICIER.

TABLE XIX

| Theor. Mass (Da) | Peptide Sequence | SEQ ID NO: | Observed Ratios* | | | | |
|---|---|---|---|---|---|---|---|
| 1318.72 | (K)NQVSLTCLVK(G) | 1 | <u>1.23</u> | <u>1.64</u> | <u>2.29</u> | <u>4.22</u> | <u>8.9</u> |
| 1328.63 | (R)AMDTGLYICK(V) | 2 | 0.88 | <u>0.62</u> | <u>1.43</u> | <u>0.61</u> | <u>0.7</u> |
| 1374.63 | (R)AMDTGLYICK(V) | 2 | 0.95 | 1.39 | 2.01 | 4.31 | 8.2 |
| 1642.79 | (R)GIASFVCEYASPGK(A) | 3 | 0.96 | 1.39 | 1.86 | 3.68 | 10 |
| 2296.11 | <u>(R)TPEVTCVVVDVSHEDPEVK(F)</u>** | 4 | 1.02 | 1.52 | 2.3 | 4.62 | 8.6 |
| 2958.35 | (R)WQQGNVFSCSVMHEALHNHYTQK(S) | 5 | 0.88 | <u>0.84</u> | <u>1.61</u> | <u>2.88</u> | <u>2.9</u> |
| 2974.35 | (R)WQQGNVFSCSVMHEALHNHYTQK(S) | 5 | <u>0.72</u> | 1.59 | 2.18 | 5.01 | 11 |
| | Mean of the Observed Ratio | | 1.04 | 1.47 | 2.09 | 4.41 | 9.38 |
| | Expected Ratio | | 1 | 1.5 | 2 | 5 | 10 |
| | Standard Deviation | | 0.04 | 0.1 | 0.19 | 0.56 | 1.2 |
| | % Error | | 4 | 1.83 | 4.38 | 11.9 | 6.25 |

In TABLE XIX, *indicates observed ratio values. Underlining indicates poor quality or overlapping peaks. These values were not included in the statistical calculation.

From these data, it was illustrated that the observed ratios closely reflect the expected ratios of light to heavy ICIER labeled peptides, especially when mass peaks that give very weak intensity or overlap with other mass peaks were excluded. The percentage error of quantitation using the ICIER approach is less than 12% for all ratios which is very accurate in contrast to densitometry. Furthermore, the ICIER approach is also capable of quantifying multiple proteins in a single sample, gel band or spot since the quantitation is based on peptides with known sequence identity.

From these data, it was also concluded that with the use of a mixture of light and heavy ICIER, an exact number of cysteine residues contained in each detected MS peak can be determined based on the presence or absence of the isotopically labeled pairs without extra sample manipulation (see TABLE XX). This additional information can be readily used with peptide masses for a more constrained peptide mass mapping to give confident protein identification. This is particularly useful when dealing with more than one protein in an analysis or only a limited number of mass peaks.

TABLE XX

Identification of the exact number of cysteine residues in each MS peaks

| Experimental Mass (Da) | Exact Number of Cysteines | Sequence of Cysteine-Containing Peptides Derived from CTLA4-IgG: | SEQ ID NO: |
|---|---|---|---|
| 587.1578 | 0 | | |
| 951.2411 | 0 | | |
| 1286.6826 | 0 | | |
| 1318.6902 | 1—light | (K)NQVSLTC*LVK(G) | 1 |
| 1325.6597 | 1—heavy | (K)NQVSLTC**LVK(G) | 1 |
| 1344.7691 | 1—light | (R)AM*DTGLYIC*K(V) | 2 |
| 1351.6682 | 1—heavy | (R)AM*DTGLYIC**K(V) | 2 |
| 1481.7472 | 0 | | |
| 1642.8055 | 1—light | (R)GIASFVC*EYASPGK(A) | 3 |
| 1649.9140 | 1—heavy | (R)GIASFVC**EYASPGK(A) | 3 |
| 1677.6275 | 0 | | |
| 1689.7607 | 0 | | |
| 1807.8651 | 0 | | |
| 1872.8749 | 0 | | |
| 2296.0488 | 1—light | (R)TPEVTC*VVVDVSHEDPEVK(F) | 4 |
| 2303.1326 | 1—heavy | (R)TPEVTC**VVVDVSHEDPEVK(F) | 4 |
| 2958.8857 | 1—light | (R)WQQGNVFSC*SVMHEALHNHYTQK(S) | 5 |
| 2965.5758 | 1—heavy | (R)WQQGNVFSC**SVMHEALHNHYTQK(S) | 5 |
| 2974.3697 | 1—light | (R)WQQGNVFSC*SVM*HEALHNHYTQK(S) | 5 |
| 2981.1270 | 1—heavy | (R)WQQGNVFSC**SVM*HEALHNHYTQK(S) | 5 |
| 3336.6515 | 0 | | |

Abbreviations: C*, cysteine residue labeled by light ICIER; C**, cysteine residue labeled by heavy ICIER; M*, oxidized methionine.

All publications cited in this specification are incorporated by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for enhancing identification and relative quantitation of proteins and peptides using mass spectrometry (MS), said method comprising the steps of:

(a) reducing disulfide bonds of a first sample from a biological mixture containing proteins and peptides;

(b) labeling proteins and peptides in the first sample with a reagent which comprises a thiol-specific reactive group attached to a guanidino group via a linker, said linker can be differentially labeled;

(c) separating the proteins and peptides from the sample;

(d) digesting the proteins to provide a mixture containing digestion peptides and peptides from the first sample; and (e) subjecting the peptides of (d) to quantitative MS analysis and protein identification.

2. The method according to claim 1, wherein the peptides of (d) are subjected to matrix-assisted laser desorption/ionization (MALDI)-MS.

3. The method according to claim 1, wherein the thiol-specific reactive group is selected from the group consisting of α-haloacetyl (—X—CH$_2$CO—, X=I, Br, or Cl) and a meleimide group having a structure selected from the group consisting of:

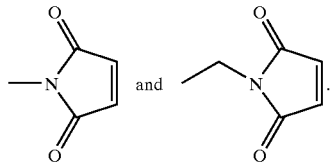

4. The method according to claim 1, wherein the linker comprises an alkyl chain having three to eight carbon atoms, optionally substituted with one or more amido groups, carboxy groups, or amino groups.

5. The method according to claim 1, wherein the proteins and peptides are further subjected to peptide mass mapping, said method further comprising the steps of:

labeling proteins and peptides in a second sample with said reagent having heavy stable isotopes, and mixing the first and second samples prior to the separation step, wherein the reagent in the labeling step of the first sample contains light stable isotopes.

6. The method according to claim 5, wherein the reagent is selected from the group consisting of:

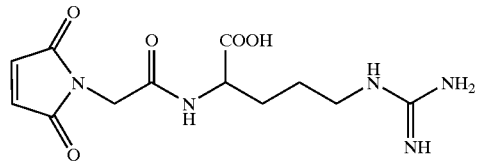

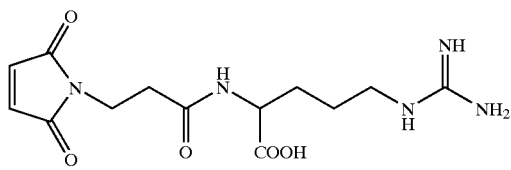

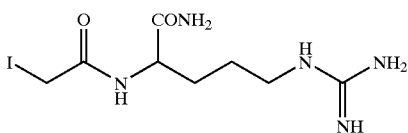

and

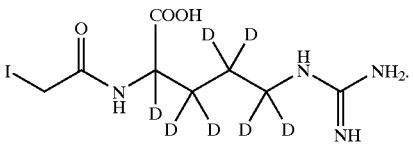

7. The method according to claim 5, wherein the separation step is performed using one dimensional or two dimensional polyacrylmide gel electrophoresis (1D or 2D-PAGE), or liquid chromatography.

8. The method according to claim 1, wherein the linker in the reagent of step (b) contains a substitution of four to twelve atoms with a stable isotope.

9. The method according to claim 8, wherein the linker contains seven stable isotopes.

10. The method according to claim 8, wherein the substitution comprises substituting hydrogen atoms with deuterium.

11. The method according to claim 1, wherein the digestion step is performed in-gel or in solution.

12. The method according to claim 11, wherein the digestion step is performed using trypsin.

13. A method for preparing peptides for matrix-assisted laser desorption/ionization mass spectrometry (MALDI-MS) and subsequent data analysis, said method comprising the steps of:

(a) reducing disulfide bonds of proteins from biological samples;

(b) labeling proteins in a first sample with a first reagent which comprises a thiol-specific reactive group attached to a guanidino group via a linker, said linker is differentially labeled with light stable isotopes;

(c) labeling proteins in a second sample with a second reagent which comprises a thiol-specific reactive group attached to a guanidino group via a linker, said linker is differentially labeled with heavy stable isotopes;

(d) mixing the first and second labeled samples;

(e) separating the proteins from the mixture and;

(f) digesting the proteins, thereby providing peptides ready for MALDI-MS analysis and protein identification.

* * * * *

UNITED STATES PATENT AND TRADEMARK OFFICE
CERTIFICATE OF CORRECTION

PATENT NO. : 6,905,879 B2 Page 1 of 1
APPLICATION NO. : 10/044708
DATED : June 14, 2005
INVENTOR(S) : Yongchang Qiu et al.

It is certified that error appears in the above-identified patent and that said Letters Patent is hereby corrected as shown below:

Column 1, lines 24 and 25, "inter alia" should read -- *inter alia* --.

Column 2, line 26, "thereof" should read -- thereof. --.

Column 4, lines 1 through 9 (between formulas), insert -- and --.

Column 4, lines 51, "Reagent C¢:" should read -- Reagent C': --.

Column 5, line 38, "in situ" should read -- *in situ* --.

Column 6, lines 9 and 10, "de novo" should read -- *de novo* --.

Column 6, line 46, "37° C" should read -- 37°C --.

Column 8, line 31, "Reagents of the Invention" should read -- REAGENTS OF THE INVENTION --.

Signed and Sealed this

Twelfth Day of September, 2006

JON W. DUDAS
*Director of the United States Patent and Trademark Office*